United States Patent [19]

Patel

[11] 4,331,161
[45] May 25, 1982

[54] PATIENT SENSOR CONTINUITY DETECTOR

[75] Inventor: Anilbhai S. Patel, White Plains, N.Y.

[73] Assignee: Healthdyne, Inc., Marietta, Ga.

[21] Appl. No.: 45,562

[22] Filed: Jun. 4, 1979

Related U.S. Application Data

[63] Continuation-in-part of Ser. No. 40,614, May 17, 1979, abandoned.

[51] Int. Cl.³ .............................................. A61B 5/00
[52] U.S. Cl. .................................... 128/736; 128/1 B; 128/399
[58] Field of Search ............... 128/1 B, 399, 804, 734, 128/736, 908, 303.13, 303.14

[56] References Cited

U.S. PATENT DOCUMENTS 3,789,853 2/1974 Reinhard ............................. 128/399
3,895,635 7/1975 Justus et al. ..................... 128/303.13
3,933,157 1/1976 Bjurwill et al. ................ 128/303.14
4,034,740 7/1977 Atherton et al. ................... 128/1 B

FOREIGN PATENT DOCUMENTS 1139927 11/1962 Fed. Rep. of Germany ....................... 128/303.13

OTHER PUBLICATIONS

Agate, F. J. et al., *Pediatrics*, May 1963, pp. 725-733.
United States F.D.A., paper dated May 22, 1978.

*Primary Examiner*—Lee S. Cohen
*Attorney, Agent, or Firm*—Schwartz, Jeffery, Schwaab, Mack, Blumenthal & Koch

[57] ABSTRACT

A device detects a discontinuity in the communication of a sensor with a patient by detecting separation of the sensor from the patient. An alarm responds to the detected separation of the sensor from the patient to signal the discontinuity in the sensor operation. The device is particularly useful with a patient warming device which is responsive to the patient's temperature as sensed by the sensor for controlling the heat applied to the patient.

4 Claims, 5 Drawing Figures

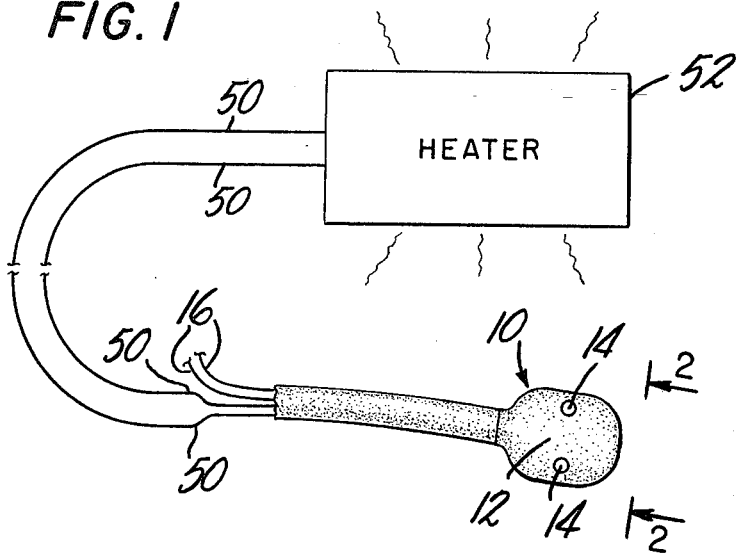
FIG. 1
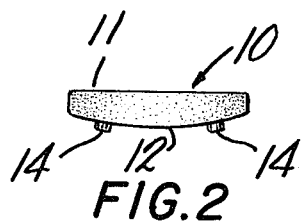
FIG. 2
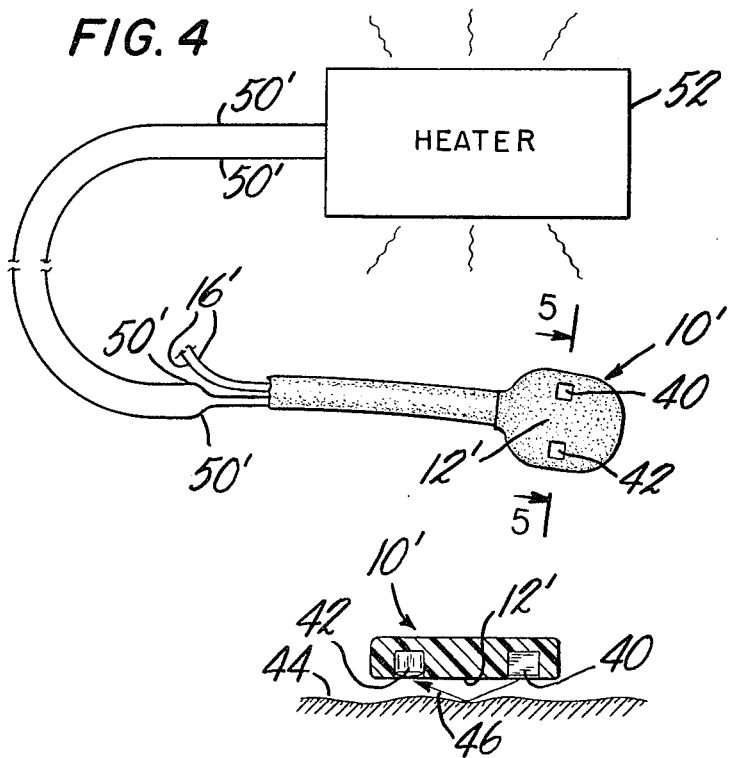
FIG. 4
FIG. 5

PATIENT SENSOR CONTINUITY DETECTOR

CROSS-REFERENCE TO RELATED APPLICATION

This application is a continuation in part of copending but concurrently abandoned U.S. patent application Ser. No. 040,614 filed May 17, 1979.

BACKGROUND OF THE INVENTION

The invention relates to a device for detecting discontinuities in the communication of a sensor with a patient.

Modern medical practice uses a variety of sensors juxtaposed with a patient for sensing a condition of the patient. For example, heart beat sensors, brain wave sensors and skin temperature sensors are now widely used. Each of these sensors is brought into close proximity with the patient so as to penetrate slightly into the patient, be in surface, skin contact with the patient, or be slightly spaced from the patient by a tape or gel, all of which are described here as juxtaposing the sensor with the patient.

If the sensors separate from the patient to a nonjuxtaposed position, they will lose sensing communication with the patient. The sensors therefore are usually adhesively taped or strapped to the patient to try to hold them in their operative, juxtaposed position. The arrangement for holding the sensor on the patient cannot be overly secure, however, in order to provide ready disconnect to allow emergency services to be provided to the patient, to allow the patient to be transferred, to provide for patient comfort in avoiding excessive pressures and allowing body movement and, of course, to allow final removal of the sensor.

A still further problem particularly limits the adhesive taping of sensors to infants. The infants skin is very fragile. The adhesive on the tape thus tends to tear the infant's skin when it is made sufficiently adherant to resist detachment from the infant's movement and then is removed for servicing the infant. The adhesive for taping sensors to infants thus cannot be as strong as would be desired merely for holding the sensor on the infant. As a result of all these limitations on holding a sensor on both adults and infants, the sensor can be dislodged by patient movement or other inadvertent action.

Sometimes the resulting loss of sensor communication with the patient is indicated by the corresponding loss of sensor function. For example, with a heart beat sensor, separation of the sensor from the patient stops the sensing of heart beats. An alarm on the heart beat monitor connected to the sensor will then be triggered, but the alarm will not indicate whether the absence of a sensed heart beat has occurred because the patient's heart has stopped, or because the sensor has lost communication with the patient. When the patient is unconscious, valuable time can then be lost in checking for the patient's heart beat to determine the cause of the alarm.

In other applications there may be even less indication of the loss of sensor communication with the patient. For example, the care of burn victims and infants often includes a radiant heater for maintaining the patient's body temperature. The heater is controlled with a skin temperature sensor to supply heat to the patient as indicated by the patient's skin temperature. If the sensor becomes dislodged from the patient's skin, overheating or underheating the patient can result from the consequent discontinuity in the communication between the sensor and patient. The over- or underheating, moreover, cannot be detected from the operation of the heater as previously proposed, except at extremes of over- or underheating the patient because of the wide range of heating conditions which are required for variations in patient and ambient temperature.

Thus, for example, the normal body movement of an infant in an incubator or other early-care arrangement including a radiant heater for heating the infant can dislodge a temperature sensor which has been taped to the infant's skin only strongly enough to avoid damage to infant's skin when the sensor is intentionally removed. The dislodged sensor will then sense an ambient temperature to which the heater responds. The heater then can seriously over- or underheat the infant. Instructions to the infant not to remove the sensor are clearly as ineffective in avoiding the problem as response from the infant to the over- or underheating is in detecting it.

SUMMARY OF THE INVENTION

It is therefore an object of the invention to provide a device for signaling a discontinuity in the communication of a sensor with a patient.

To this end the invention provides a device for signaling at least partial separation of a sensor from juxtaposition with the patient which separation can cause a discontinuity in the communication of the sensor with the patient. The device has a detector for detecting the separation of the sensor from the patient and an alarm responsive to the detected separation to signal the resulting communication discontinuity between the sensor and patient.

In one preferred embodiment, the detector comprises a pair of probes spaced apart on the sensor and electrically insulated from each other across their separation on the sensor. The probes are positioned on the sensor for contact with the patient's skin when the sensor is juxtaposed with the patient for sensing a patient's condition. The probes are also connected to an electrical supply so that the detector passes a minute electrical current through the patients' skin between the probes. If the sensor is then dislodged from juxtaposition with the patient and thus loses sensing communication with the patient, at least one probe separates from the patient and an alarm responds to the resulting interruption in the skin current to signal the discontinuity in sensor communication.

In another preferred embodiment, the detector comprises a photodiode on the side of the sensor which is juxtaposed with the patient. The body of the sensor is opaque to shield the photodiode from light while the diode is sandwiched against the patient by the juxtaposed sensor. If the sensor is then dislodged from the patient, ambient or local light reaches the photodiode, and an alarm responds to the light detection in the diode to signal the separation of the sensor from the patient and concurrent discontinuity in the sensor communication with the patient.

The device thus allows a sensor to be attached to a patient only as firmly as allows for patient comfort and protection from injury such as, for example, injury to the fragile skin of an infant when excessively adhesive tape holding a sensor on the infant is intentionally removed. If even normal patient movement then occassionally dislodges the sensor from the patient, the alarm in the device signals the separation of the sensor from the patient and the resulting, at least potential loss of sensor communication with the patient.

The detector in the device is independent of the patient-sensing elements in the sensor and independent of a monitor responsive to the sensed patient function. The device thus indicates that the cause of the alarm is separation of the sensor from the patient as distinct from a dysfunction of the sensor, monitor or patient. With a heart beat sensor, for example, an alarm from the device will clearly suggest that sensor separation from the patient and not a dysfunction of the patients heart caused simultaneous alarms from the device and an alarm unit on a heart beat monitor connected to the sensor. This operation is enhanced by a slight delay common in the heart beat monitor alarms to accomodate normal irregularities in the patient's heart beat. A similar delay in the discontinuity detecting device of this invention is not needed so that the separation alarm can preceed the heart beat alarm to indicate more clearly that the alarms are due to separation of the sensor from the patient.

Each of the preferred embodiments has a further advantage in being able to indicate partial separation of the sensor from the patient and thus only possible or insipient loss of sensor communication with the patient. Each thus serves as an early-warning device for indicating that adjustment of the sensor attachment is needed before any actual discontinuity in communication has occured. With the first described, probe embodiment, separation of only one probe from the patient is sufficient to interrupt the skin current and trigger the alarm. Partial retention of the sensor on the patient with the other probe firmly in contact with the patient's skin thus does not defeat the alarm signal. The other, photodiode preferred embodiment operates similarly. A mere crack separation of one edge of the sensor from the patient is sufficient to let light reach the diode and trigger the alarm. An actual or insipient discontinuity in sensor communication from a loose sensor-patient juxtaposition thus triggers the alarm in both preferred embodiments.

Both preferred embodiments also lend themselves to another feature of the invention. The mechanics of patient movement often curve the patient's skin or body surface at the sensor. The sensor should thus be made with a small area of patient juxtaposition to avoid bridging concave curves in the underlying patient surface or mere tangential juxtaposition on convex surfaces. Either of these partial engagements with the patient could cause the sensor to lose proper communication with the patient either directly from the partial separation from the patient or indirectly by loosening the tape or strap attaching the sensor to the patient. Making the sensor with a small patient interface avoids these problems, and the spaced probes or single photodiode can be made correspondingly small so as not to increase the size of the sensor undesireably.

DESCRIPTION OF THE DRAWINGS

These and other features of the invention will now be described in greater detail with reference to drawings of the preferred embodiments which illustrate but do not limit the invention and in which:

FIG. 1 is a bottom view of a sensor having the probes of one preferred embodiment;

FIG. 2 is an elevation of the sensor in FIG. 1;

FIG. 4 is a bottom view of a sensor having the photodiode of another preferred embodiment; and FIG. 5 is an elevation, partly in section, of the sensor shown in FIG. 4.

DESCRIPTION OF THE PREFERRED EMBODIMENTS

Figure 3:
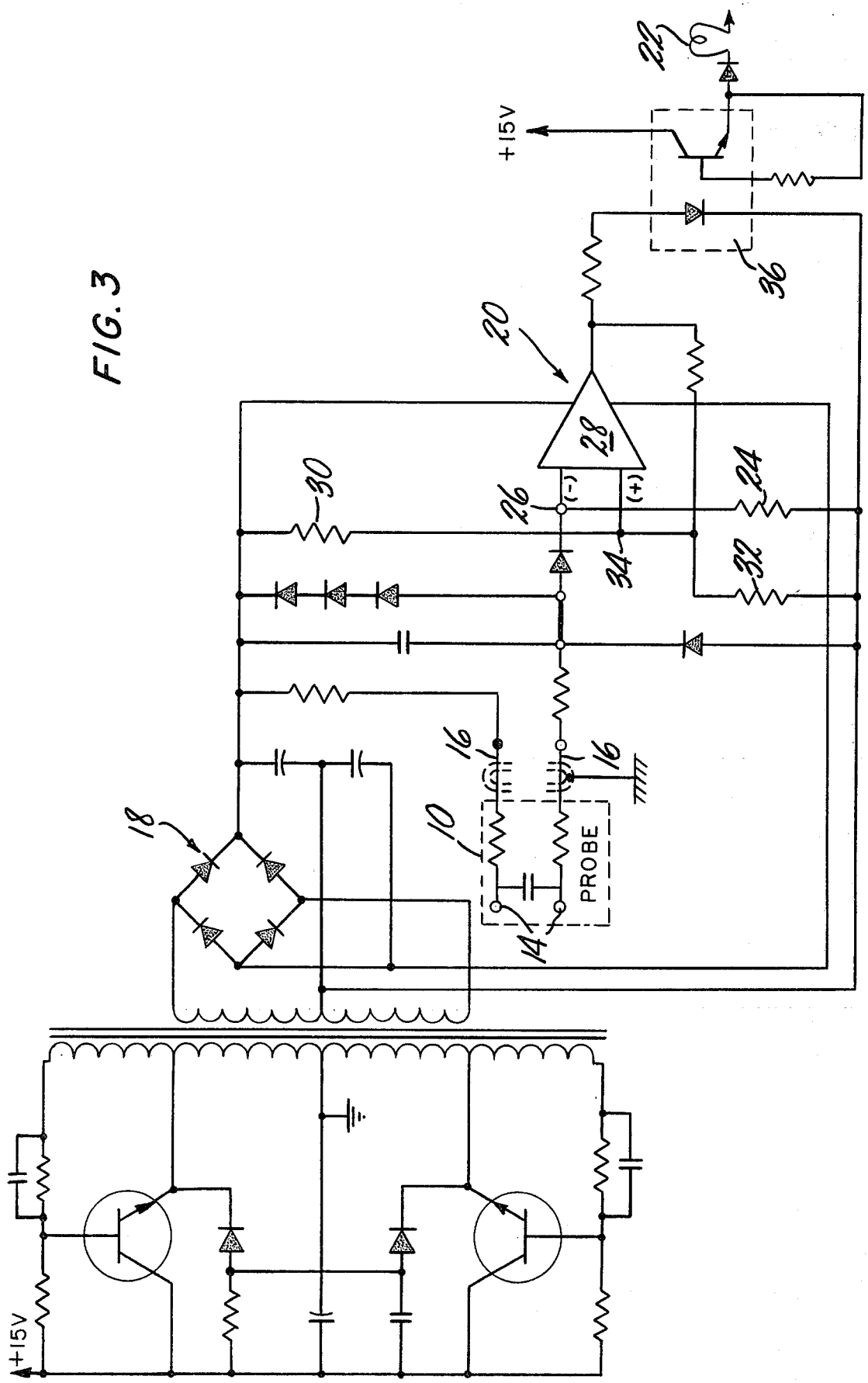
FIG. 3 is a schematic of a detector and alarm for the sensor of FIG. 1.

FIGS. 1 and 2 show a temperature sensor 10 of a known type having a thermister (not shown) in the body of the sensor connected by leads 50 to a device 52 for heating the patient (not shown) in response to the patients skin temperature when the sensor is in operative contact or juxtaposition with the patient's skin. A plain, outer surface 11 of the sensor can be adhesively taped to the patient in accord with the common practice for operatively attaching such sensors to patients. The opposite, inner surface 12 is then juxtaposed with the patient's skin.

The inner surface 12 has a pair of spaced probes 14 which contact the patients skin when the sensor is operatively juxtaposed on the patient. The probes are connected by leads 16 to an electric power supply at 18 shown in FIG. 3. The power supply is carefully designed with a plurality of current limiting arrangements to then pass a minute current between the probes through the patient's skin when the probes are in operative contact with the patient.

FIG. 3 also shows an alarm device at 20 which responds to an interruption of the minute current between the probes with an alarm signal which is illustrated here as activating an alarm speaker 22. The current between the probes will be interrupted by separating either of probes 14 from the patient's skin as will occur if the sensor separates from the patient and thus loses temperature sensing communication with the patient.

Returning to FIGS. 1 and 2, the sensor 10 is about 5/16" (0.79 cm) in maximum transverse dimensions on the opposite surfaces 11,12 and about 3/16" (0.48 cm) thick. This small size makes the sensor easier to attach to small patients such as infants, but more importantly, assists in maintaining operative juxtaposition of the sensor on the patient. Normal body movement of the patient will convexly or concavely curve the patient's skin under the sensor. Keeping the transverse surface dimensions of the sensor small thus helps minimize partial separation of the sensor from the patient by bridging the concave skin curves or tangentially engaging only part of convex skin curves. If sufficiently prolonged, such partial separation can interfere with the temperature sensing function of the sensor by providing insufficient heat-transfer contact between the sensor and the patient. Of at least equal importance, however, the sensor bridging or tangentially engaging the patient can mechanically stretch or separate the tape or other arrangement holding the sensor on the patient. The resulting loosening of the sensor holding arrangement could then lead undesireably to premature separation of the sensor from the patient.

The sensor preferably encases or pots the thermister inside the sensor body to prevent damage. The sensor body is then preferably formed of a good thermal conductor to optimize temperature sensing communication with the patient.

The sensor body surface 12 must also electrically insulate the probes 14 from each other so that current does not flow across the sensor surface. For these two thermal transmission and electrical insulation functions, the sensor is preferably formed of alumina ($Al_2O_3$) or a temperature conductive, insulative glass filled fiberglass printed circuit board type material commonly designated G 10.

The sensor surface 12 is shown in FIG. 2 to be slightly curved convexly with the probes 14 projecting to about the altitude of the curve of about 1/32" (0.08 cm). The combination of the curve and projecting probes is intended to help maintain contact between the probes and the patient's skin during normal body movement without poking into the patient sufficiently to cause patient discomfort.

Returning to FIG. 3, the sensor 10 is seen to include an AC shunt capacitor and DC current-limiting series resistors connected to each probe 14. These along with familiar isolation, clamp and current-limiting arrangements in the power supply at 18, safely limit the current through the patient's skin to less than $10^{-6}$ amps without excessive transients from power supply variations or component failures. Of particular note in the power supply current-limiting safety devices is a very large resistor 24 of about 50 to $150 \times 10^6$ ohms in the probe-skin circuit.

The large safety resistor 24 also forms part of the alarm device 20. The resistor 24 is connected to one input terminal 26 of an operational amplifier 28 in a potential dividing arrangement across the input power in the probe-skin circuit path. The operational amplifier is arranged as a Schmitt trigger with another pair of potential dividing resistors 30,32 connected to another input terminal 34 and across the same input power as the first potential dividing arrangement for common mode rejection of false triggering signals. When the potential at input terminal 26 changes by separating at least one probe 14 from the patient's skin to interrupt the current in the probe-skin path, the Schmitt trigger changes state to send a logic level alarm signal to an output device 36. The output device 36, which is shown schematically, responds to the logic level signal with an alarm power signal to speaker 22 for an audible alarm sound.

A SECOND PREFERRED EMBODIMENT

FIGS. 4 and 5 show another preferred embodiment of a sensor 10' which is substantially similiar in outward configuration to the sensor shown in FIGS. 1 and 2. In the embodiment of FIGS. 4 and 5, however, a pair of diodes 40, 42 are flush mounted in the patient-juxtaposed surface 12'.

Diode 40 is a photodiode or other photo-detector and diode 42 is a light-emitting diode (LED). FIG. 5 schematically shows how these diodes operate to detect separation of the sensor 10' from the patient's skin 44, the sensor being opaque to shield the diodes from light except at patient surface 12'. When the sensor separates even slightly from the skin at any angle thereto, some rays from the LED 42 which is an omni-directional point-like source will reflect from the patient's skin to the photodiode 40. The photodiode response to this light then triggers an alarm. The alarm and power circuits for the diodes are not shown, however, because both are well within the skill in the art.

The two diode arrangement is preferred because the tape or strap which holds the sensor to the patient may shield the photodiode from ambient light at least until the sensor fully separates from the patient, or there may be no ambient light as at night to trigger the photodiode. In many hospital environments, however, the ambient nightlight may be sufficient to trigger a photodiode and the tape or strap may be sufficiently transparent to transmit even this nightlight to the patient's skin at the sensor surface 12' when the sensor separates even slightly at only one edge from the patient's skin. In this case, it may then be preferred to provide only the photodiode.

Cost and simplicity are two obvious advantages of the alternative photo-diode-alone arrangement. Another less-obvious advantage, however, is in retrofitting existing sensors with the sensor separation alarm device of this invention. In such retrofitting applications, a very small photo-diode chip on leads 16' can merely be inserted under existing light-opaque sensors with little patient discomfort and a minimum of difficulty.

The single photodiode and other alternatives and variations are intended to be within the scope of the invention defined by the following claims. The preferred, alternative and variational embodiments all cooperate with a variety of patient-care systems which have a sensor for sensing a patient function or condition, and especially those which control the patients' care in response to the sensed condition. For example, radiant heaters for warming burn victims or infants are usually responsive to a temperature sensor of the type described for controlling the heat supplied to the patient. If such a sensor loses sensing communication with the patient by separating from the patients' skin, as for example under normal patient movement, the heater will then respond to the ambient heat at the dislodged sensor with results which can seriously over- or under-heat the patient. The alarm of the invention, however, will indicate the loss of proper sensor function to alert corrective action.

I claim:

1. A device for detecting a discontinuity in the communication of a temperature sensor with a patient, comprising:
   (a) a patient temperature sensor adapted to be juxtaposed with the skin of the patient and adapted to actuate and control a heater for warming the patient,
   (b) a detector at the sensor for detecting at least partial separation of the sensor from said juxtaposition with the patient, said detector comprising a pair of electrically conducting probes extending from the surface of the sensor and spaced apart and electrically insulated from each other on the sensor for contact with the patient's skin when the sensor is operatively juxtaposed with the patient;
   (c) circuit means including electrical supply means connected to the probes for passing a minute electrical current between the probes through the patient's skin, and
   (d) an alarm within said circuit means and operatively connected to said electrical supply means and to said probes, said alarm being actuated in response to an interruption in the current between the probes consequent to separation of either probe from the skin of the patient, thereby indicating detection of the discontinuity.

2. A device as in claim 9, wherein the sensor has a surface adapted to be adjacent to the patient's skin when the sensor is operatively juxtaposed with the patient, and wherein the probes project slightly from the sensor surface for electrical contact with the patients' skin.

3. A device as in claim 2 wherein the sensor surface has maximum dimensions across the surface of about 5/16".

4. A device as in claim 2 wherein the sensor surface curves convexly to a maximum elevation between the probes approximately equal to the projection of the probes from the surface.

* * * * *